Figure 1:
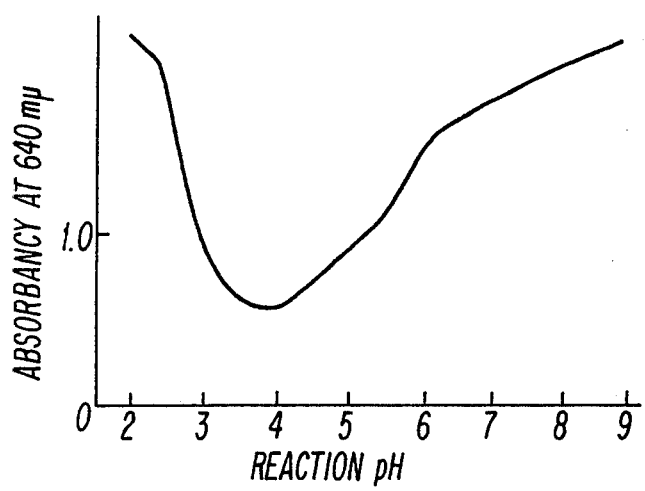

United States Patent [19]

Yoshida et al.

[11] 4,258,134

[45] Mar. 24, 1981

[54] NOVEL HYALURONIDASE BMP-8231 AND PRODUCTION THEREOF

[75] Inventors: Keizo Yoshida, Ibaraki; Takashi Fujii, Sekimachi; Hiroyuki Kikuchi, Hachiouji, all of Japan

[73] Assignee: Fujisawa Pharmaceutical Co., Ltd., Osaka, Japan

[21] Appl. No.: 35,719

[22] Filed: May 3, 1979

[30] Foreign Application Priority Data

May 11, 1978 [JP] Japan .................................. 53/56313

[51] Int. Cl.³ ............................................... C12N 9/26
[52] U.S. Cl. ...................................... 435/201; 435/886
[58] Field of Search ........................................ 435/201

[56] References Cited

U.S. PATENT DOCUMENTS

| 3,728,223 | 4/1973 | Kaneko et al. | 435/201 |
| 3,945,889 | 3/1976 | Mima et al. | 435/201 |

FOREIGN PATENT DOCUMENTS 2018608  5/1970  France .

OTHER PUBLICATIONS

Neufeld et al., editors, Methods in Enzymology, vol. VIII, pp. 654–662, (1966).
Chemical Abstracts 71, 46855b, (1969).
Chemical Abstracts 82, 40537e, (1975).
Chemical Abstracts 76, 11008d, (1972).
Chemical Abstracts 85, 76359z, (1976).

*Primary Examiner*—Lionel M. Shapiro
*Attorney, Agent, or Firm*—Oblon, Fisher, Spivak, McClelland & Maier

[57] ABSTRACT

Hyaluronidase obtained from Streptomyces koganeiensis has the following characteristics:
  (a) Acts as an endo B-hexosaminidase
  (b) Degrades hyaluronic acid but not chondroitin sulfate A, C, or chondroitin
  (c) Optimum pH around 4.0
  (d) Stable pH range 4.0–11.3
  (e) Optimum temperature around 60° C.
  (f) Stable a temperature below 60° C.
  (g) Stable against proteolytic enzymes

4 Claims, 6 Drawing Figures

NOVEL HYALURONIDASE BMP-8231 AND PRODUCTION THEREOF

This invention relates to a new hyaluronidase, hereinafter referred to as hyaluronidase BMP-8231. More particularly, this invention relates to a new hyaluronidase BMP-8231 and to the production thereof.

It is to be noted that "Hyaluronidase" is a general term for an enzyme, which is, in common, capable of cleavaging glucosidic bonds of hyaluronic acid and, to a variable degree, of some other acid mucopolysaccharides of connective tissue. As to the utility of hyaluronidase, it is a spreading factor, diffusing factor, etc., and has been used as a spreading agent to promote diffusion and hasten absorption in medical use and used in antibiotic solution for the treatment of animal disease, e.g. bovine mastitis in veterinary use (cf. The Merck Index, Eighth Edition), and also has been used as an analytical reagent in biochemical field. Further, it was reported that some of the hyaluronidase was shown to produce significant reduction in myocardial infarct size (cf. Science Vol. 194, pages 199-200, October 1976).

Up to now, various types of specific hyaluronidase have been known to be produced from the various animal tissues and secretions (e.g. testicle, etc.) and the culture broth of pathogenic bacteria (e.g. *Staphylococcus aureus*). However, the production of hyaluronidase by the pathogenic bacteria was industrially unavailable, and also the hyaluronidases produced from the bacterial and animal source were shown to become labile and unstable when the purifications proceeded, and accordingly the stable and highly potent hyaluronidase could not be provided due to its property of unstability.

Then, recently, an attempt to provide a stable hyaluronidase was conducted, and it was reported that a new specific strain of the genus Streptomyces, i.e. *Streptomyces hyalurolyticus* nov. sp. (Deposit number: FERM-P No. 427) produced the stable hyaluronidase (cf. Biochim. Biophys. Acta. 198 (1970) 607-609) and Japanese Patent Publication No. 1195/71 published on Jan. 12, 1971). However, this new hyaluronidase is still unstable due to inactivation on proteolytic enzyme, and accordingly can not be said to be sufficient for use as an analytical reagent used for the analysis of biological samples containing proteolytic enzyme and further it may be inactivated by proteolytic enzyme in a body so that the medical activity thereof may be decreased.

Under the state of the arts as stated above, the inventors of this invention have conducted extensive studies for searching a characteristic and improved hyaluronidase, and as the results, the present inventors have found out a new characteristic hyaluronidase BMP-8231 in the culture broth of *Streptomyces koganeiensis* nov. sp. and established industrial production of this enzyme. Hyaluronidase BMP-8231 of this invention, as compared with prior each of hyaluronidases, is characterized by higher stability, non-susceptibility to the proteolytic enzyme, much higher enzymatic potency and the like, and further characteristics of this hyaluronidase per se will be apparent from the description below. Accordingly, it is one object of this invention to provide a new enzyme, hyaluronidase BMP-8231 having higher stability, non-susceptibility to the proteolytic enzyme, much higher enzymatic potency. Another object of this invention is to provide a process for preparation of hyaluronidase BMP-8231 by fermentation of a hyaluronidase BMP-8231 producing strain belonging to the genus Streptomyces in a nutrient medium.

Hyaluronidase BMP-8231 of this invention can be produced by culturing a hyaluronidase BMP-8231 producing strain belonging to the genus Streptomyces, particularly *Streptomyces koganeiensis* in a nutrient medium.

The Microorganism

One of the microorganism which can be used for the production of hyaluronidase BMP-8231 of this invention is a strain of *Streptomyces koganeiensis* No. 8231, which was newly isolated from a soil sample collected in Koganei City, Tokyo, Japan.

A culture of the living organism has been deposited with and added to a permanent stock culture collection of the American Type Culture Collection under the number ATCC 31394 on Apr. 25, 1978. Further, a culture of the said organism has also been deposited with Fermentation Research Institute, Agency of Industrial Science and Technology, Japan under the number FERM-P No. 4480 on Apr. 14, 1978.

It is to be understood that the production of the new hyaluronidase BMP-8231 of this invention is not limited to the use of the particular organism described herein, which is given for illustrative purpose only. That is, this invention also includes the use of any mutants which are capable of producing hyaluronidase BMP-8231, including natural mutants as well as artificial mutants which can be produced from the described organism in conventional manner, e.g. physical treatment such as radiation with X-ray, ultraviolet-ray, etc., chemical treatment with N-methyl-N'-nitro-N-nitrosoguanidine, 2-aminopurine, nitrogen mustard oils, etc., and the like.

*Streptomyces koganeiensis* No. 8231 has the following morphological, cultural and biological and physiological characteristics.

1. Morphological characteristics Microscopic observations were made on cultures which were grown on sucrose-nitrate agar, glycerin-asparagine agar, yeast-malt extract agar, inorganic salts-startch agar and oatmeal agar at 28° C. for 10-14 days.

(1) Type of branching of spore-forming hyphae:
Monopodial branching
(2) Form of spore-forming hyphae:
Spiral
(3) Numbers of spores:
10-30 spores
(4) Surface appearance and size of spore:
Smooth
0.2-0.9×1.0-1.5 micron
(5) Existence of zoospore:
Not observed
(6) Existence of sporangium:
Not observed 2. Cultural characteristics The following observations were made on cultures which were grown on various media at 28° C. for 10-14 days.

| Medium | Aerial mass color | Reverse side of colony | Soluble pigment |
|---|---|---|---|
| Sucrose-nitrate agar | none | colorless - pale yellow, small colonies | none |
| Glucose-asparagine agar | none | pale yellow - yellow, slightly wrinkled, small | none |

| Medium | Aerial mass color | Reverse side of colony | Soluble pigment |
| --- | --- | --- | --- |
| Glycerin-asparagine agar | very thin, white | colonies colorless - pale yellow, small colonies | none |
| Starch-inorganic salts agar | thin, gray | pale yellow - yellowish brown, small colonies | none |
| Tyrosine agar | very thin, white | pale yellowish brown, small colonies | none |
| Nutrient agar | none | colorless - cream colored, very small colonies | none |
| Yeast-malt extract agar | none | colorless - pale yellow, wrinkled colonies | none |
| Oatmeal agar | none | pale yellow - yellow, flat, small colonies | none |
| Glucose-peptone gelatin stab | none | colorless - pale yellow, wrinkled colonies | none |
| Milk | none | faint growth | none |
| Peptone-yeast iron agar | none | colorless - cream colored, very small colonies | none |

3. Biological and physiological properties (1) Temperature requirements (on Bennett's agar slants)

Growth from 15° C. to 40° C. (Optimum 28° C.)

(2) Liquefaction of gelatin (on glucose-peptone gelatin stab)

positive (3) Hydrolysis of starch (on starch-inorganic salts agar)

positive (4) Action on milk no coagulation, no peptonization (5) Production of melanin (on tyrosine agar, peptone-yeast iron agar and tryptone-yeast broth)

negative (6) Utilization of various carbon compounds (on Pridham-Gottlieb basal agar medium)

| | |
| --- | --- |
| L - Arabinose | + |
| D - Xylose | + |
| D - Glucose | + |
| D - Fructose | + |
| D - Galactose | + |
| Sucrose | + |
| Glycerin | + + |
| Inositol | + |
| Lactose | + |
| L - Rhamnose | + |
| Maltose | + |
| Raffinose | + |
| D - Mannitol | + |
| D - Mannose | + |
| Salicin | − |
| Cellulose | − |

+ +; very good utilization,
+; good utilization,
−; no utilization

As a result of looking up the strain possesing the characteristics mentioned above by referring to the literatures, i.e. "Bergey's Manual of Determinative Bacteriology" Eighth Edition (1975), "The Actinomycetes" Vol. II(1961) written by S. A. Waksman and "The International Streptomyces Project Reports" written by E. B. Shirling and D. Gottlieb [cf. International Journal of Systematic Bacteriology Vol. 18, pages 69 and 279(1968), Vol. 19, page 391(1969) and Vol. 22, page 265(1972)], *Streptomyces vastus*, *Streptomyces canarius* and *Streptomyces nigellus* have been detected as relatively analogous characteristics to those of the strain No. 8231 of this invention. The strain No. 8231, however, is different from these analogous species in the following respects.

*Streptomyces vastus*

*Streptomyces vastus* forms aerial mycelia on yeast-malt extract agar and oatmeal agar. Reverse side of colonies shows grayish green on yeast-malt extract agar and pale blue on oatmeal agar and starch inorganic salts agar.

*Streptomyces canarius*

*Streptomyces canarius* forms aerial mycelia on yeast-malt extract agar and oatmeal agar and produces yellow—yellowish green soluble pigment.

*Streptomyces nigellus*

*Streptomyces nigellus* forms aerial mycelia on yeast-malt extract agar and oatmeal agar and reverse side of colonies shows gray—brownish gray.

From the above differences between the strain No. 8231 of this invention and the three known species, it should be said that the strain No. 8231 belongs to a different species from the above three species. Incidentally, the strain No. 8231 is a absolutely different from *Streptomyces hyalurolyticus* which is known as a hyaluronidase producing strain as mentioned hereinabove in view of differences of forms of aerial mycelia and chromogenecity.

In view of the results of the above observation, the strain No. 8231 can be judged as a new species belonging to the genus Streptomyces and accordingly has been designated as *Streptomyces koganeiensis* No. 8231.

PRODUCTION OF HYALURONIDASE BMP-8231

The hyaluronidase BMP-8231 is produced by culturing a hyaluronidase BMP-8231 producing strain belonging to the genus Streptomyces, such as *Streptomyces koganeiensis* No. 8231 in a nutrient medium.

In general, hyaluronidase BMP-8231 is produced by culturing a hyaluronidase BMP-8231 producing strain in a nutrient medium containing assimilable sources of carbon and of nitrogen, preferably under aerobic conditions (e.g. shaking culture, submerged culture, etc.).

The preferred sources of carbon in the nutrient medium are carbohydrates such as glucose, fructose, glycerin and starch. Other sources which may be included are lactose, arabinose, xylose, dextrin, molasses and the like.

The preferred sources of nitrogen are yeast extract, peptone, gluten meal, cottonseed meal, soybean meal, corn steep liquor, dried yeast, etc., as well as inorganic and organic nitrogen compounds such as ammonium salts (e.g. ammonium nitrate, ammonium sulfate, ammonium phosphate, etc.), urea, amino acid and the like.

The carbon and nitrogen sources, though advantageously employed in combination, need not be used in their pure form because less pure materials which contain traces of growth factors and considerable quantities of mineral nutrients, are also suitable for use. When desired, there may be added to medium such mineral salts as calcium carbonate, sodium or potassium phosphate, sodium or potassium chloride, magnesium salt, and the like. If necessary, especially when the culture medium is foamed remarkably, a defoaming agent such as liquid paraffin, higher alcohol, plant oil, mineral oil and silicones may be added.

As conditions for the production in massive amounts, submerged aerobic cultural condition is preferred for the production of the hyaluronidase BMP-8231. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the hyaluronidase BMP-8231. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. As the medium, in which the vegetative inoculum is produced, there can be used the substantially same as or somewhat different medium from medium utilized for main production of the hyaluronidase BMP-8231.

Agitation and aeration of the culture mixture may be accomplished in a variety of ways. Agitation may be provided by a propeller or the similar mechanical agitation equipment, by revolving or shaking the fermenter, by various pumping equipment or by the passage of sterile air through the medium. Aeration may be effected by passing sterile air through the fermentation mixture.

The fermentation is usually conducted at a temperature about between 20° C. and 40° C., preferably around 30° C., for a period of 50 hours to 100 hours, which may be varied according to the fermentation conditions and scale.

Thus produced hyaluronidase BMP-8231 can be recovered from the culture medium by conventional means which are commonly used for the recovery of other fermentation products such as enzymes.

In general, most of the hyaluronidase BMP-8231 produced are found in the culture filtrate, which is obtained by filtering the culture broth, and accordingly the hyaluronidase BMP-8231 can be isolated and purified from the filtrate in a conventional manner. That is, for example, after the filtrate is concentrated under reduced pressure, the concentrate is subjected to salting-out techniques with neutral salts (e.g. ammonium sulfate, etc.) and/or precipitation with organic solvents (e.g. acetone, etc.) to give precipitates, and said precipitates are optionally dialyzed overnight against water or buffer solution. Then, the dialyzed sample is subjected to a column chromatography using adsorbents (e.g. DEAE-cellulose, CM-cellulose, etc.) and/or a gel filtration with Sephadex (e.g. Sephadex G-25, Sephadex G-50, Sephadex G-100, etc.) (trade name, Pharmacia A B). The fractions thus obtained containing hyaluronidase BMP-8231 are evaporated in vacuo or lyophilized to give purified hyaluronidase BMP-8231. For obtaining the purer hyaluronidase BMP-8231, it is preferable to repeat the above techniques. Further, it is to be noted that the techniques as explained above are only for the illustrative purpose of one mode of this invention, and accordingly the other techniques conventionally used for the isolation and purification of enzyme in enzyme science are applied to isolation and purification of the hyaluronidase BMP-8231.

The hyaluronidase BMP-8231 as obtained according to the aforementioned process possesses the following biochemical properties;

(a) Type of Action
Endo β-hexosaminidase
(b) Substrate Specificity
Degradable: Hyaluronic acid
Not degradable: Chondroitin sulfate A, chondroitin sulfate C and chondroitin.
(b) Effect of pH
(i) Optimum pH: around pH 4.0

As shown in FIG. 1 of accompanying drawings, optimum pH of hyaluronidase BMP-8231 is around pH 4.0. Enzyme activities at various pH were measured by the following method.

To 0.15% aqueous sodium hyaluronate solution (0.1 ml) were added an aqueous solution of hyaluronidase BMP-8231 (4 μg/ml)(0.1 ml) and Veronal buffer solution (0.8 ml) adjusted to the prescribed pH. The mixture was incubated at 60° C. for 30 minutes. After the reaction mixture was cooled with water, a serum solution (4 ml) as mentioned in the Determination Method I given below was added thereto. The resultant mixture was stirred sufficiently and allowed to stand at ambient temperature for 30 minutes and then turbidity of the mixture at 640 mμ was measured. The results are shown in FIG. 1.

(ii) Stable pH range: pH 4.0–pH 11.3

Figure 2:
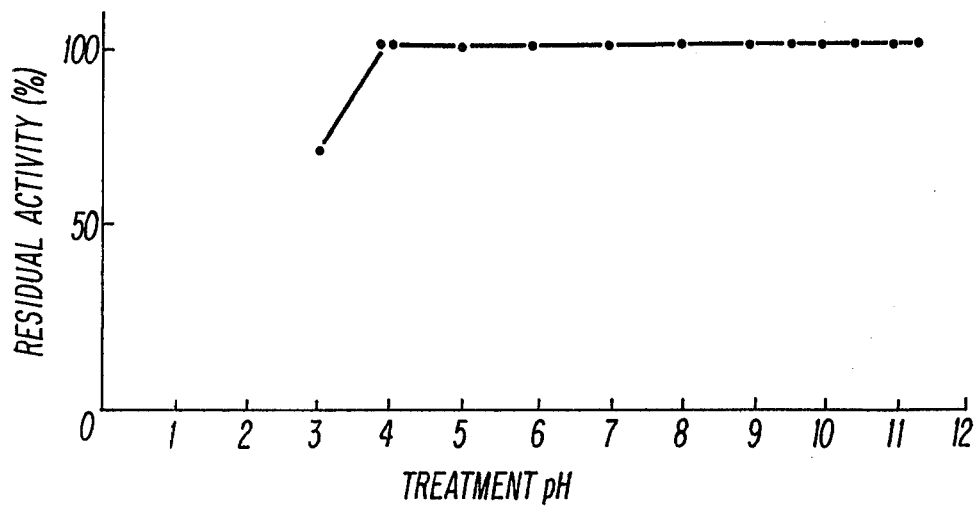

As shown in FIG. 2 of accompanying drawings, hyaluronidase BMP-8231 is stable in a broad range of pH of pH 4.0–11.3. The stability test was conducted by the following method.

Hyaluronidase BMP-8231 was immersed in each of the following various buffer solutions at 37° C. for 16 hours.

pH 2.1–6.0: Clark-Lubs buffer solution
pH 5.9–7.9: $KH_2PO_4$-NaOH buffer solution
pH 7.9–10.0: $H_3BO_4$-KCl-NaOH buffer solution
pH 10.5–11.3: HCl-$Na_2CO_3$ buffer solution Then, the residual enzyme activity of hyaluronidase BMP-8231 was determined according to the Determination Method I given below. The results are shown in the FIG. 2.

(d) Effect of Temperature
(i) Optimum temperature: Around 60° C.

Figure 3:
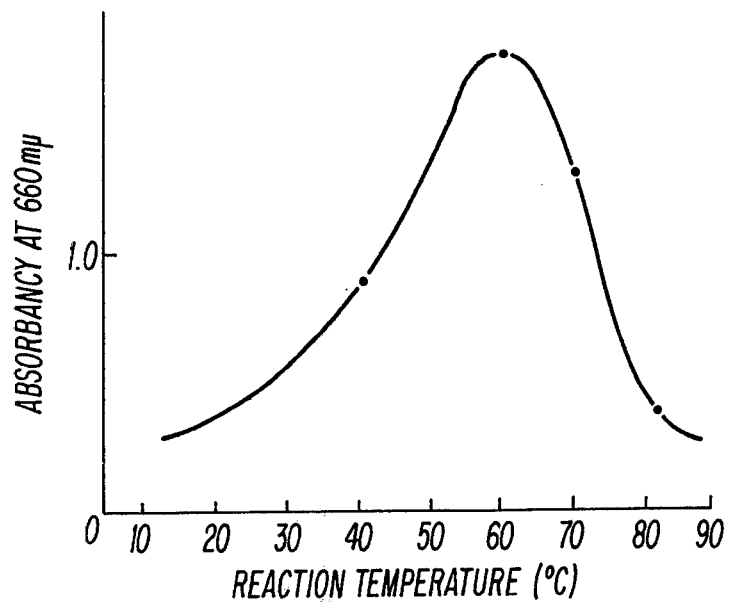

As shown in FIG. 3 of accompanying drawings, optimum temperature of hyaluronidase BMP-8231 is around 60° C.

Effect of temperature on enzyme activity of the hyaluronidase BMP-8231 was tested by the following method.

After the hyaluronidase BMP-8231 was incubated in citrate buffer solution (pH 6.0) at the prescribed temperature for 30 minutes, the enzyme activity of the hyaluronidase was measured according to the Determination Method II given below. The results are shown in FIG. 3.

(ii) Stable temperature range: Below 60° C.

Figure 4:
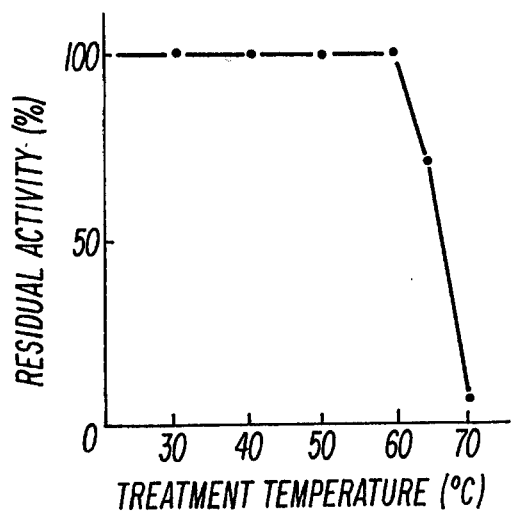

As shown in FIG. 4 of accompanying drawings, stable temperature range of hyaluronidase BMP-8231 is below 60° C. Stability of the enzyme to the temperature was tested by the following method.

The hyaluronidase BMP-8231 was incubated in a phosphate buffer solution (pH 7.0) at the prescribed temperatures for 30 minutes. The residual enzyme activity of the hyaluronidase was measured according to the Determination Method I. The results are shown in FIG. 4.

(e) Stability against proteolytic enzyme
After the prescribed amount of a proteolytic enzyme, Pronase E (trade mark, made by Kaken Chemical Co., Ltd.) was subjected to contact with hyaluronidase BMP-8231 (20 μg) in phosphate buffer solution (pH 7.0) at 37° C. for the prescribed hours, the residual enzyme activity of hyaluronidase BMP-8231 was measured according to Determination Method II given below. The results are shown in FIG. 5.

On the other hand, hyaluronidase "Amano" (10 μg) (trade mark, made by Amano Pharmaceutical Co., Ltd., Japan, a hyaluronidase produced by *Streptomyces hyalurolyticus* nov. sp.) was treated with Pronase E and the residual activity thereof was determined in substantially the same manners as described above. The results are shown in FIG. 6.

Figure 5:
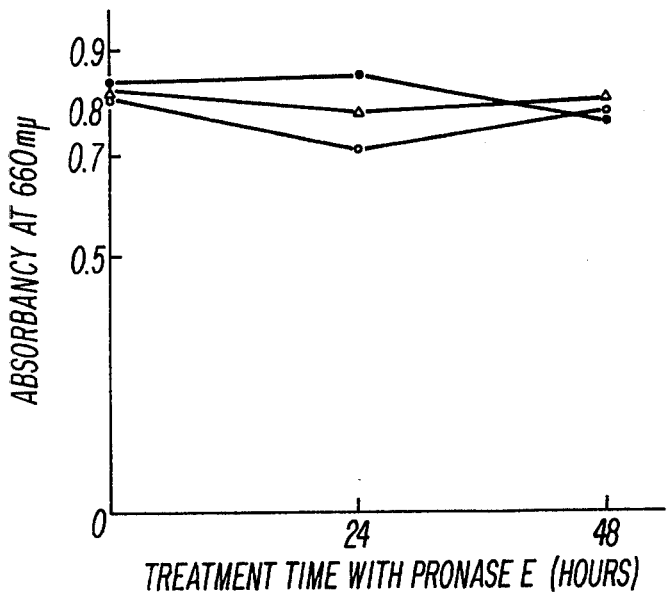
Figure 6:
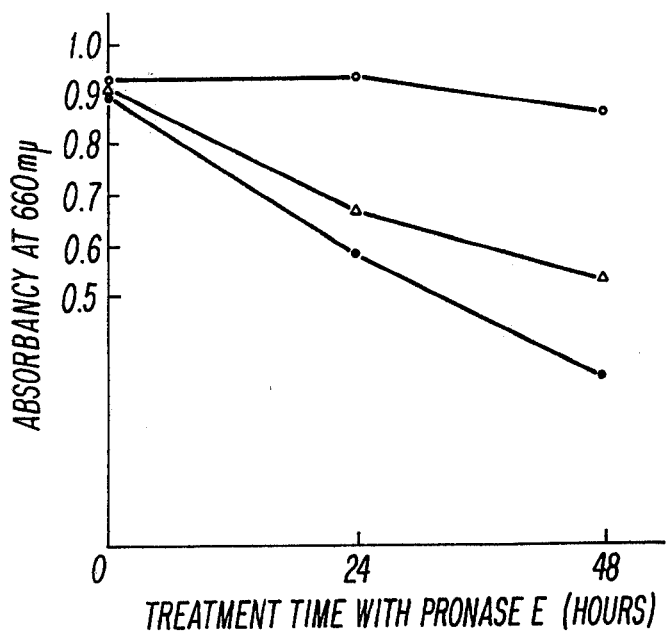

As to the marks in the FIGS. 5 and 6, it is to be noted that "o—o", "Δ—Δ" and "o—o" indicate the residual activities in case of the treatment with Pronase E (500 μg), treatment with Pronase E (200 μg) and non-treatment with Pronase E, respectively.

From the above results, it was clearly observed that the hyaluronidase BMP-8231 was not inactivated by treatment with the proteolytic enzyme on one hand and the hyaluronidase "Amano" was remarkably inactivated by treatment with the proteolytic enzyme on the other hand.

(f) Effect of antiserum (i) Preparation of antiserum

Emulsion prepared by mixing a solution of the hyaluronidase BMP-8231 (1.5 mg) in phosphate buffer solution (pH 7.0)(1 ml) and complete adjuvant (Difco) was intracutaneously injected into four pads of a rabbit. Two weeks after the injection, the same emulsion as mentioned above was intracutaneously injected again into the back of the rabbit. One month after the second injection, blood samples were collected from the rabbit, allowed to stand overnight at ambient temperature and then centrifuged at 10,000 r.p.m. x one hour to given antiserum against hyaluronidase BMP-8231.

(ii) Precipitation reaction of hyaluronidases with antiserum against hyaluronidase BMP-8231

Hyaluronidase BMP-8231 reacted with antiserum against hyaluronidase BMP-8231. On the other hand, hyaluronidase "Amano" did not react with the said antiserum at all. Both of the above enzymes did not react with normal serum of the rabbit at all.

(iii) Effect of antiserum on hyaluronidase activity

The antiserum against hyaluronidase BMP-8231 inhibited the enzyme activity of hyaluronidase BMP-8231. On the other hand, the said antiserum did not inhibit hyaluronidase "Amano". Further, the enzyme activity of both of the above enzymes were not inhibited with normal serum of the rabbit.

Enzyme activity of hyaluronidase can be measured by the following method.

Determination Method I (a) Preparation of solutions (i) Acetate buffer solution

Potassium acetate (14 g) and glacial acetic acid (20.5 ml) were dissolved in sufficient water to make one liter.

(ii) Phosphate buffer solution

Sodium biphosphate (2.5 g), anhydrous sodium orthophosphate (1.0 g) and sodium chloride (8.2 g) were dissolved in sufficient water to make one liter.

(iii) Serum solution

To calf-serum (100 ml) was added the above acetate buffer solution (900 ml). After adjusting the serum solution to pH 3.1 with hydrochloric acid, said serum solution was stored at 4° C. When used, the serum stock solution was diluted with 3 volumes of the above acetate buffer solution.

(iv) Hyaluronic acid solution

Sodium hyaluronate (Sigma) was dissolved in water (500 μg/ml). The resultant solution was diluted with one volume of the above phosphate buffer solution.

(b) Reaction

To the above hyaluronic acid solution (0.5 ml) was added an enzyme solution (0.5 ml) of the prescribed amount of hyaluronidase dissolved in the above phosphate buffer. After incubated at 37° C. for 30 minutes, the reaction mixture was immediately cooled with water. To the resultant mixture was added the serum solution (4 ml) and stirred sufficiently. After the mixture was allowed to stand at ambient temperature for 30 minutes, turbidity of the mixture at 640 mμ was measured.

Determination Method II (a) Preparation of solutions (i) Hyaluronic acid solution Sodium hyaluronate (Sigma) was dissolved in 1/10 M citrate buffer solution (pH 6.0) (1 mg/ml).

(ii) Aqueous sodium carbonate-potassium cyanide solution

Sodium carbonate (5.3 g) and potassium cyanide (0.65 g) were dissolved in sufficient water to make one liter.

(iii) Aqueous ferric ion solution

Ferric ammonium sulfate (1.5 g) and a detergent, Duponol (1 g)(trade mark, made by E I DUPONT DE NEMOURS & CO.) were dissolved in sufficient 0.05 N sulfuric acid to make one liter.

(b) Reaction

To the above hyaluronic acid solution (0.5 ml) was added a solution (0.1 ml) of the prescribed amount of hyaluronidase dissolved in phosphate buffer solution as mentioned in Determination Method I. After incubating at 37° C. for 30 minutes, the reaction mixture was allowed to stand in a boiling water bath for 2 minutes in order to stop the reaction and then immediately cooled with water. To the resultant mixture were added the above aqueous sodium carbonate potassium cyanide solution (0.3 ml) and 0.05% aqueous potassium ferricyanide solution (0.3 ml). The mixture was heated again in a boiling water bath for 9 minutes and then cooled with water. To the resultant mixture were added 1 N hydrochloric acid (0.1 ml) and the above aqueous ferric ion solution (1 ml). The mixture was allowed to stand at ambient temperature for 15 minutes and then the optical density of the mixture at 660 mμ was measured.

From the above observation, it should be said that hyaluronidase BMP-8231 of this invention is a new hyaluronidase different from the known hyaluronidases in animal tissues and cultured broths of the microorganisms mentioned above.

The following Example is given for the purpose of illustrating this invention.

EXAMPLE

An aqueous medium (80 ml) comprising 3% starch, 1% cottonseed meal, 1% gluten meal, 1% dried yeast, 0.1% $K_2HPO_4$, 0.1% $MgSO_4.7H_2O$ and 0.4% defoaming agent, Adecanol (trade mark, made by ASAHI DENKA KOGYO K.K.) was poured into each of three 500 ml, Sakaguchi flasks and sterilized at 120° C. for 20 minutes. To these media was inoculated a loopful of slant culture of *Streptomyces koganeiensis* No. 8231, respectively, and the organism was grown on a shaker at 30° C. for 3 days.

On the other hand, an aqueous medium (20 liters) comprising the same ingredients as mentioned above was poured into a 30 liters jar-fermenter and sterilized at 120° C. for 20 minutes.

To the medium was inoculated whole volume of the cultured broth as obtained above, whereafter the organisms were cultured at 30° C. for 24 hours. During the culture period, the fermentation was conducted by stirring the broth with a propeller equipment in a ratio of 300 r.p.m. and passing sterile air through the broth in a ratio of 20 l/broth/minute.

Further, an aqueous medium (150 liters) comprising the same ingredients as mentioned above was poured into 200 liters jar-fermenter and sterilized at 120° C. for 20 minutes. To the medium was inoculated 5 l of cultured broth in 30 liters jar-fermenter as obtained above and the organisms were grown at 30° C. for 3 days. During the culture period, the fermentation was conducted by stirring the broth with a propeller equipment in a ratio of 300 r.p.m. and passing sterile air through the broth in a ratio of 150 l/broth/minute.

After the completion of the culture, the cultured broth was filtered with a aid of diatomaceous earth. The filtrate was concentrated under reduced pressure to a volume of 20 liters. To the concentrate was added acetone until a final concentration thereof became 40%. Precipitates thus produced were filtered off. To the filtrate was further added acetone until a final concentration thereof became 60%. Precipitates were collected by filtration and dissolved in a small volume of water and then dialyzed overnight against water. The resulting solution was passed through a column of DEAE-cellulose ($P_1$ form). The column was washed with water and then eluted with 1/40 M phosphate buffer solution (pH 7.0) comprising 0.25 M sodium chloride. Fractions comprising the object compound were collected and concentrated under reduced pressure to a volume of 300 ml. The concentrate was desalted with a column of Sephadex G-25 and then passed through a column of CM-cellulose ($Na^+$ form). Elution of the object compound was carried out by the technique of gradient elution using 0.005 M–0.1 M acetate buffer solution (pH 5.0). The Fractions comprising the object compound were collected and concentrated under reduced pressure to a volume of 30 ml and passed through a column of Sephadex G-50. The Fractions comprising the object compound were collected and lyophilized to give powdery hyaluronidase BMP-8231 (250 mg).

As the result of determination of relative potency of enzyme activity of this hyaluronidase BMP-8231 with a hyaluronidase derived from a ovine testicle (1,100 National Formulary (NF) Hyaluronidase unit/mg) (Sigma) according to the above Determination Method I, the relative potency of enzyme activity of this powdery hyaluronidase BMP-8231 was 40,000 NF Hyaluronidase unit/mg.

We claim:

1. Hyaluronidase BMP-8231 having the characteristic of
   (a) Type of Action:
      Endo $\beta$-hexosaminidase;
   (b) Substrate Specificity:
      Degradable: Hyaluronic acid
      Not Degradable:
         Chondroitin sulfate A,
         Chondroitin sulfate C and
         Chondroitin;
   (c) Optimum pH: Around pH 4.0;
   (d) Stable pH range: 4.0–pH 11.3;
   (e) Optimum temperature: Around 60° C.;
   (f) Stable temperature range: Below 60° C.; and
   (g) Stability against proteolytic enzyme: Stable.

2. A process for preparing hyaluronidase BMP-8231, which comprises culturing a strain of *Streptomyces koganeiensis* in a nutrient medium and recovering the said hyaluronidase BMP-8231 from the cultured broth.

3. The process according to claim 2, in which the strain is *Streptomyces koganeiensis* ATCC 31394.

4. Hyaluronidase BMP-8231 obtained by the process of claim 3.

* * * * *